US012788595B2

(12) United States Patent
Shen

(10) Patent No.: US 12,788,595 B2
(45) Date of Patent: Nov. 10, 2026

(54) MODULAR KNEE JOINT

(71) Applicant: PRO LIMB INTERNATIONAL CORP., New Taipei City (TW)

(72) Inventor: Hsin-Fa Shen, New Taipei City (TW)

(73) Assignee: PRO LIMB INTERNATIONAL CORP., New Taipei City (TW)

( * ) Notice: Subject to any disclaimer, the term of this patent is extended or adjusted under 35 U.S.C. 154(b) by 430 days.

(21) Appl. No.: 18/630,716

(22) Filed: Apr. 9, 2024

(65) Prior Publication Data

US 2024/0390165 A1 Nov. 28, 2024

(30) Foreign Application Priority Data

May 22, 2023 (TW) ................................ 112118862

(51) Int. Cl.

*A61F 2/64* (2006.01)
*A61F 2/50* (2006.01)
*A61F 2/68* (2006.01)
*A61F 2/74* (2006.01)

(52) U.S. Cl.

CPC ................ *A61F 2/64* (2013.01); *A61F 2/741* (2021.08); *A61F 2/748* (2021.08); *A61F 2002/5083* (2013.01); *A61F 2002/6854* (2013.01)

(58) Field of Classification Search

CPC .. A61F 2/748; A61F 2/74; A61F 2/642; A61F 2002/5075; A61F 2002/6854; A61F 2/741; A61F 2/644; A61F 2/64; A61F 2/646; A61F 2002/648; A61F 2/604; A61F 2002/607

See application file for complete search history.

(56) References Cited

U.S. PATENT DOCUMENTS

| | | | | |
|---|---|---|---|---|
| 6,706,074 B1 * | 3/2004 | Chen | A61F 2/68 623/44 |
| 2016/0166410 A1 * | 6/2016 | Dressler | F16F 9/446 188/280 |
| 2020/0323655 A1 | 10/2020 | Shen | |
| 2023/0398002 A1 * | 12/2023 | Boiten | A61F 2/64 |

FOREIGN PATENT DOCUMENTS

| | | | |
|---|---|---|---|
| CN | 103800102 A | | 5/2014 |
| CN | 109009584 A | | 12/2018 |
| CN | 208447859 U | * | 2/2019 |

* cited by examiner

*Primary Examiner* — Katrina M Stransky
*Assistant Examiner* — Renee Florencia Nerenberg
(74) *Attorney, Agent, or Firm* — Birch, Stewart, Kolasch & Birch, LLP

(57) ABSTRACT

The modular knee joint has a connecting rod assembly, a locking assembly, and an actuating assembly. The locking assembly selectively locks the connecting rod assembly, such that the connecting rod assembly cannot pivot. When the heel of the prosthesis contacts the ground, the connecting rod assembly activates the actuating assembly, such that when the thigh and the prosthetic shank rotate at a small angle relative to each other, the locking assembly intervenes to lock the connecting rod assembly, thereby locking the actuating assembly. Therefore, the modular knee joint can maintain the resistance during the entire bending process without losing resistance after bending to a specific angle.

14 Claims, 9 Drawing Sheets

MODULAR KNEE JOINT

BACKGROUND OF THE INVENTION

1. Field of the Invention

The present invention relates to a prosthesis, especially to a modular knee joint.

2. Description of the Prior Arts

The traditional modular knee joints are single-shaft-bearing-and-actuating devices and are assembled between a thigh and a prosthetic shank of a user. When the user put the weight on the prosthetic shank and the modular knee joint, the modular knee joint activates the resistance mechanism and selectively provides the supporting force for bending. Therefore, the modular knee joint can support the user's weight, let the modular knee joint bend slowly, and facilitate the user to stand or walk by feet.

During walking, the user steps forward with the normal foot and move the center of gravity to the body on the front side. The thigh with the prosthesis on the back side pushes down against the prosthetic shank, causing the toes of the prosthesis to receive reaction force from the ground. A moment is generated on the prosthetic shank, causing the modular knee joint to bend. When the single-shaft mechanism in the traditional modular knee joint deflects due to the torque, the resistance mechanism is turned off, allowing the modular knee joint to bend significantly without resistance. Then the user swings the thigh with the prosthesis on the back side forward and thus the modular knee joint turns straight again. After the heel of the prosthesis receives reaction force from the ground and pushes against the modular knee joint, the resistance mechanism is turned on again. The resistance mechanism allows the prosthesis and the modular knee joint to support the user's weight, so the user can take the next step.

To keep the user's steps at an appropriate pace, when the thigh with the prosthesis is at the back side, the toes press down and generate a moment on the modular knee joint. The threshold of turning off the resistance mechanism must be as sensitive as possible to avoid the user's waiting for the resistance mechanism on the modular knee joint to be turned off between stepping out the normal foot and then stepping out the prosthesis. If the process of turning off the resistance mechanism is not sensitive and swift enough, the user will have an obvious stumbling feeling during walking, which will affect the pace.

However, since the traditional prosthetic knee joints are single-shaft-bearing-and-actuating device, when the body's weight applies pressure on the prosthetic shank, the heel or the toes of the prosthetic shank may activate the actuating device, and thus cause the prosthetic shank to stumble when it steps out. Therefore, it is necessary to install an elastic adjustment assembly as an anti-actuating device to reduce the sensitivity of the actuating device and the stumbling feeling when the prosthetic shank steps out. However, the elastic adjustment assembly will also reduce the sensitivity of the actuating device, resulting in incomplete startup or loss of resistance of the actuating device, which affects safety.

To overcome the shortcomings, the present invention provides a modular knee joint to mitigate or obviate the aforementioned problems.

SUMMARY OF THE INVENTION

The main objective of the present invention is to provide a modular knee joint that is configured to connect a thigh and a prosthetic shank of a user which allows the user to go down the stairs or walk on uneven ground.

The modular knee joint has an upper connecting unit, a lower connecting unit, a connecting rod assembly, a locking assembly, and an actuating assembly. The upper connecting unit is configured to connect the thigh of the user. The lower connecting unit is configured to connect the prosthetic shank and be securely mounted on the actuating assembly. The connecting rod assembly is located between the upper connecting unit and the lower connecting unit. The locking assembly selectively locks the connecting rod assembly; therefore, the connecting rod assembly is incapable of pivoting.

The actuating assembly has a first oil storage cavity, a second oil storage cavity, a first connecting channel, a second connecting channel, a movable plug, and a driven unit. The first connecting channel fluidly communicates with the first oil storage cavity and the second oil storage cavity, and the second connecting channel also fluidly communicates with the first oil storage cavity and the second oil storage cavity. The movable plug selectively blocks the first connecting channel. An end of the driven unit is connected to the connecting rod assembly, and another end of the driven unit selectively pushes the movable plug.

Wherein when the upper connecting unit and the lower connecting unit rotate with respect to each other, the driven unit and the movable plug are separated by the connecting rod assembly. Then the movable plug blocks the first connecting channel, and the locking assembly locks the connecting rod assembly at the same time. Therefore, the connecting rod assembly is incapable of pivoting, and the driven unit and the movable plug keep separated.

Through the present invention, the bending process of the modular knee joint can be maintained at a slow bending. When the user wears the modular knee joint and goes down the stairs, the bending angle of the modular knee joint can be maintained when the foot with the modular knee joint is behind, such that the modular knee joint will not lose resistance and the user will not fall on the stairs. Similarly, the user can also walk smoothly when walking on uneven ground with height differences. Therefore, if the heel contacts the ground during walking, the resistance mechanism of the modular knee joint is turned on during the full-angle bending process and the modular knee joint can be maintained at a slow bending. In contrast, the resistance mechanism of the modular knee joint is turned off when the toes contact the ground during walking.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
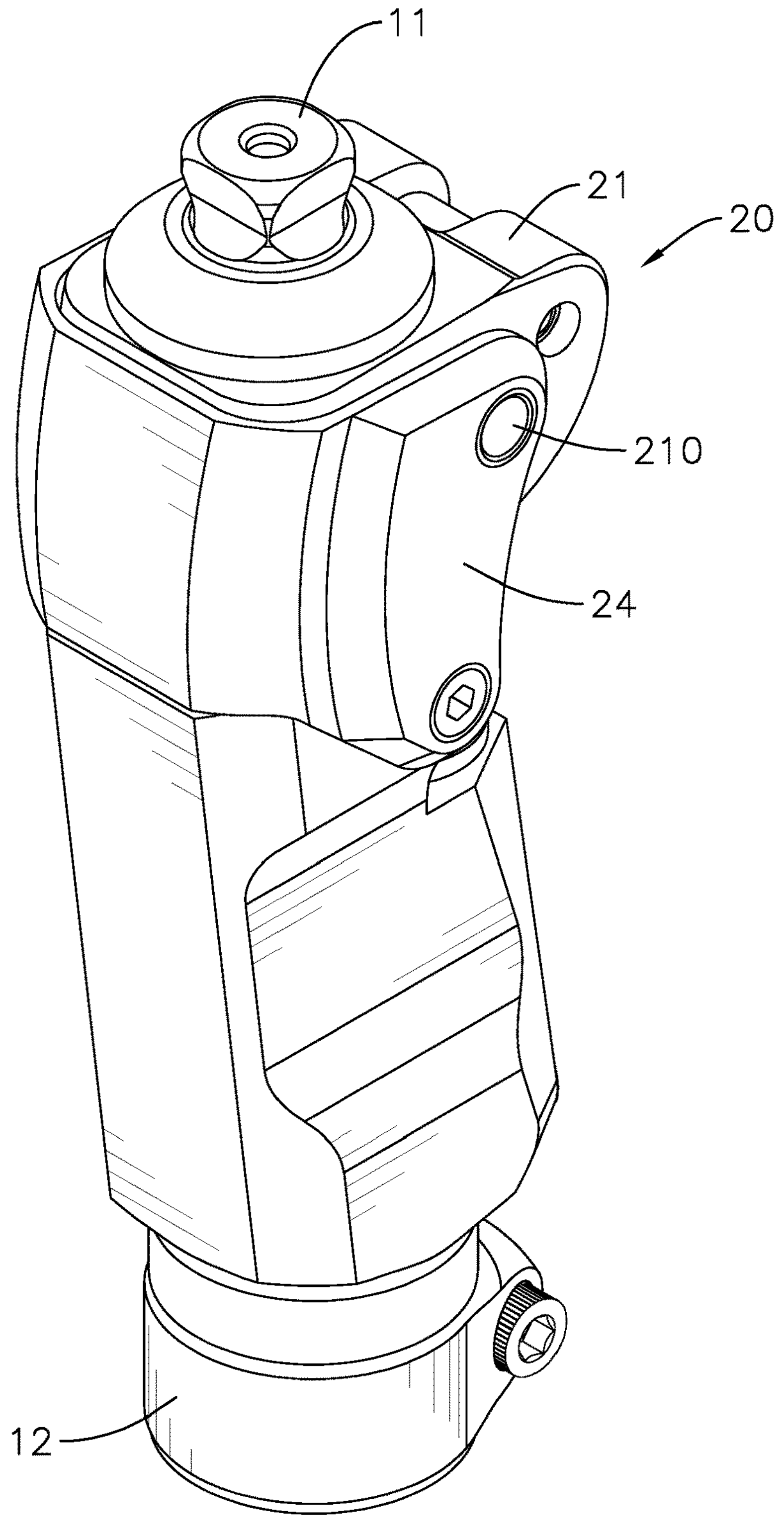
FIG. 1 is a perspective view of a modular knee joint in accordance with the present invention.
Figure 2:
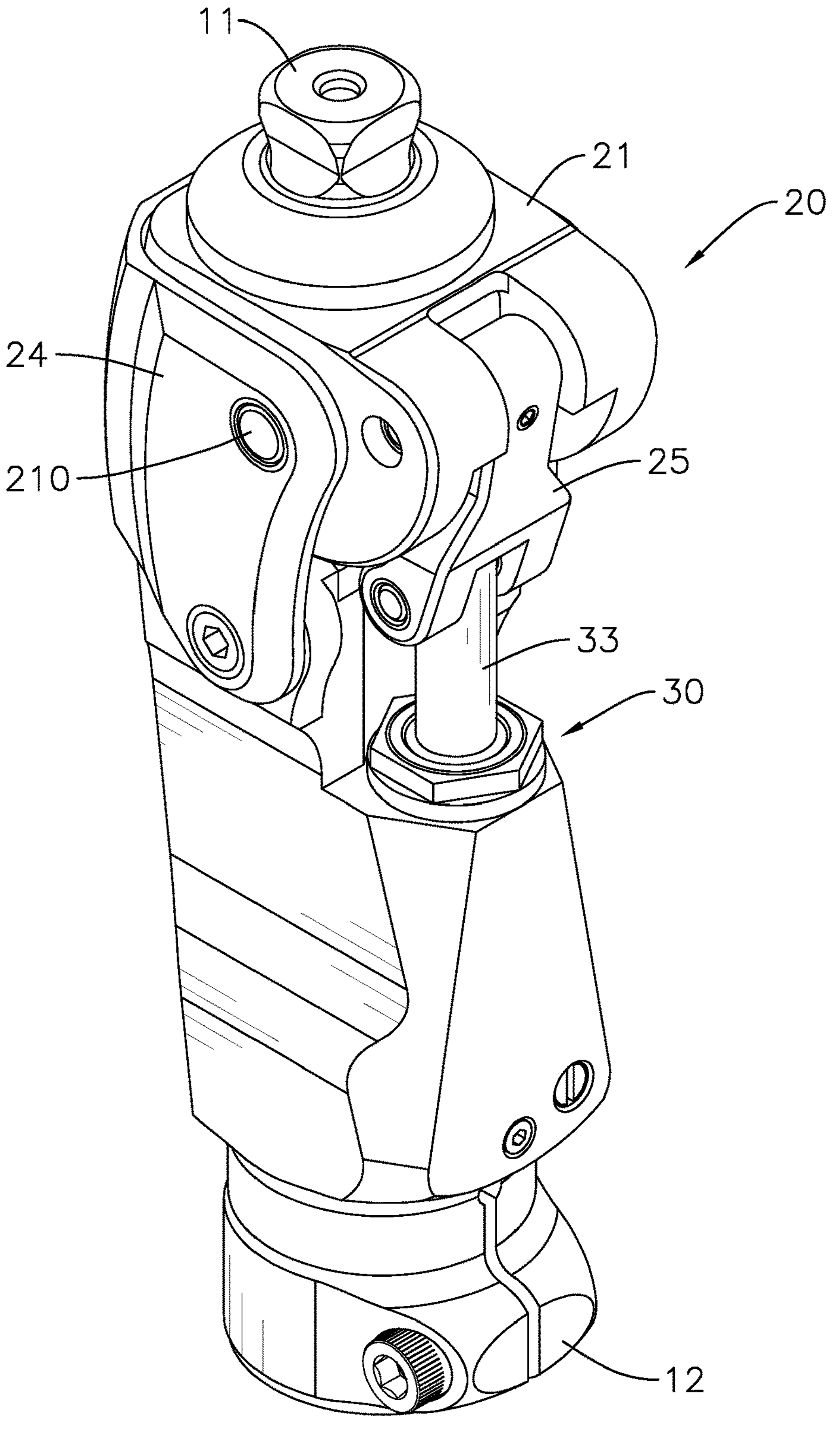
FIG. 2 is another perspective view of the modular knee joint in FIG. 1.

With reference to FIG. 1 to FIG. 4 first, a modular knee joint in accordance with the present invention has buffering effect and restriction effect and is configured to connect a thigh and a prosthetic shank of a user. The modular knee joint comprises an upper connecting unit 11, a lower connecting unit 12, a connecting rod assembly 20, an actuating assembly 30, and a locking assembly 40.

The upper connecting unit 11 is configured to connect the thigh of the user. The lower connecting unit 12 is configured to connect the prosthetic shank. The connecting rod assembly 20, the locking assembly 40, and the actuating assembly 30 are mounted between the upper connecting unit 11 and the lower connecting unit 12.

Figure 3:
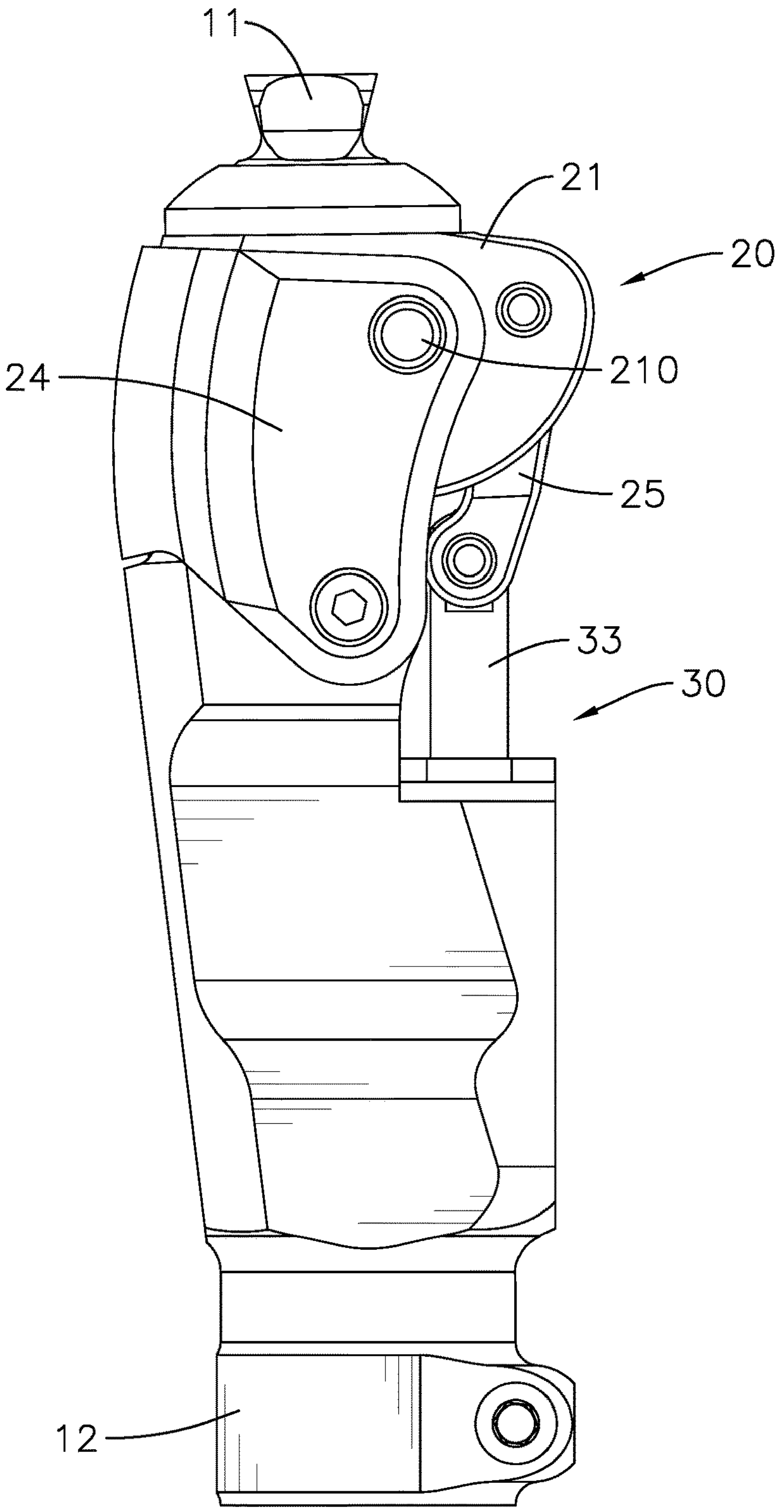
FIG. 3 is a side view of the modular knee joint in FIG. 1.
Figure 4:
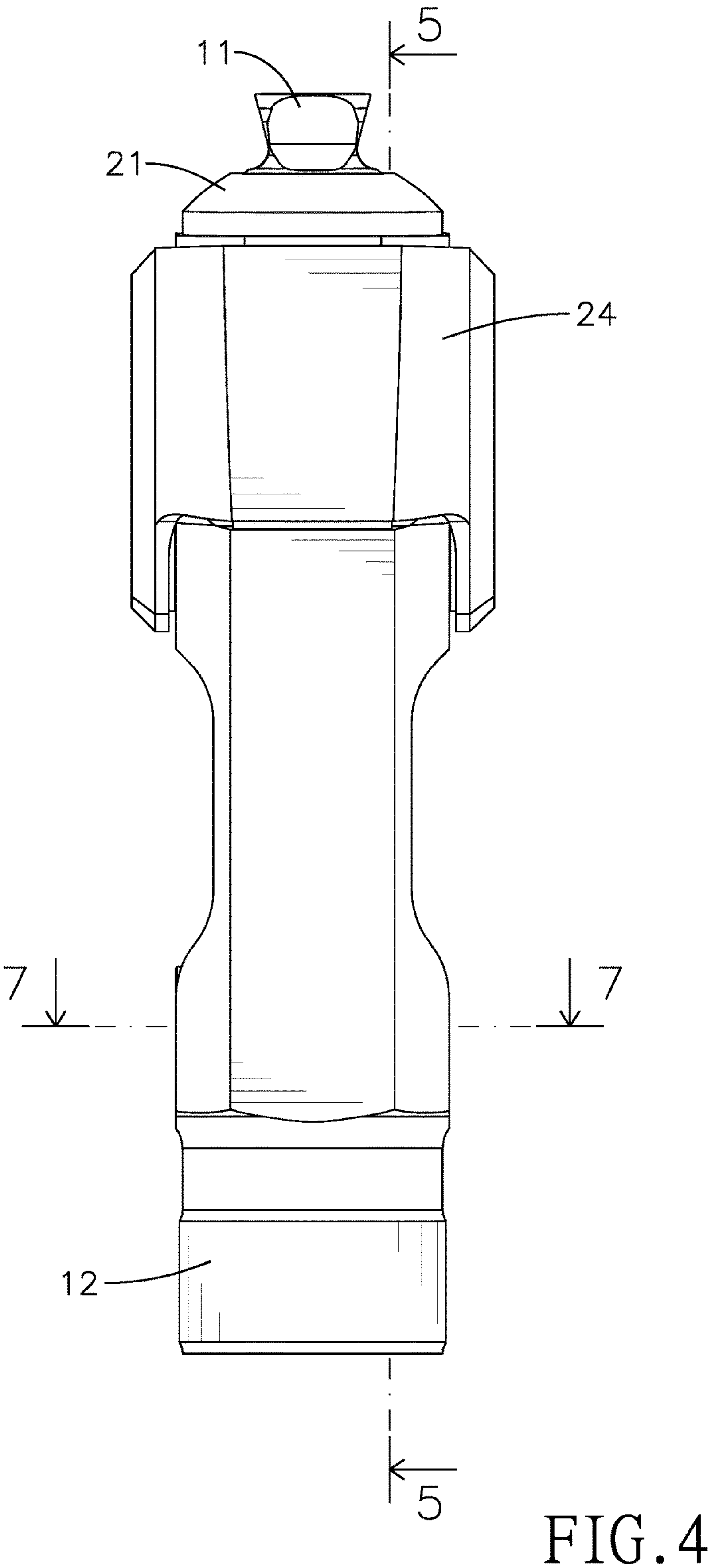
FIG. 4 is a front view of the modular knee joint in FIG. 1.
Figure 5:
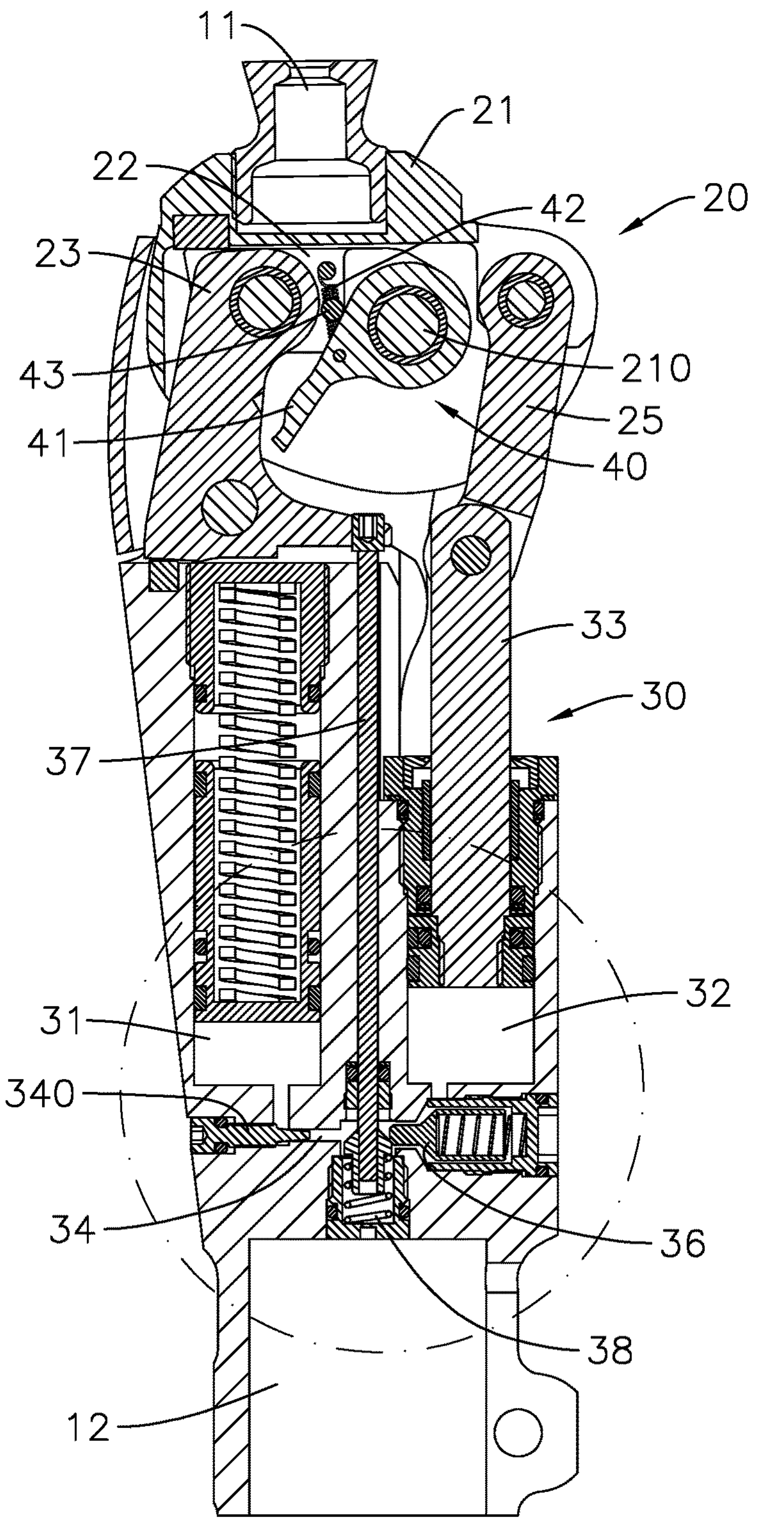
FIG. 5 is a sectional view of the modular knee joint across line 5-5 in FIG. 4.

With reference to FIG. 3 to FIG. 5, the connecting rod assembly 20 comprises a main connecting rod 21, an auxiliary connecting rod 22, a first connecting rod 23, a second connecting rod 24, and a third connecting rod 25. Wherein the main connecting rod 21, the auxiliary connecting rod 22, the first connecting rod 23, and the second connecting rod 24 form a four-bar linkage and can simulate subtle changes in the actual bending of the human knee joint. A third connecting rod 25 connects the four-bar linkage and the actuating assembly 30. The upper connecting unit 11 is securely mounted on the main connecting rod 21. The main connecting rod 21 comprises a front side, a back side, and a main pivot shaft 210. The main pivot shaft 210 is located between the front side and the back side of the main connecting rod 21. An end of the auxiliary connecting rod 22 is pivotably mounted on the main pivot shaft 210 of the main connecting rod 21.

The first connecting rod 23 comprises a first upper end and a first lower end. The first upper end is connected to the main connecting rod 21 and the first lower end is pivotably mounted on the actuating assembly 30. Precisely, the first upper end of the first connecting rod 23 is pivotably mounted on an end opposite to the main pivot shaft 210 of the auxiliary connecting rod 22. The second connecting rod 24 comprises a second upper end and a second lower end. The second upper end is connected to the main pivot shaft 210 of the main connecting rod 21 and the second lower end is pivotably mounted on the actuating assembly 30. The third connecting rod 25 comprises a third upper end and a third lower end. The third upper end is pivoted on the back side of the main connecting rod 21 and the third lower end is connected to the actuating assembly 30.

Figure 6:
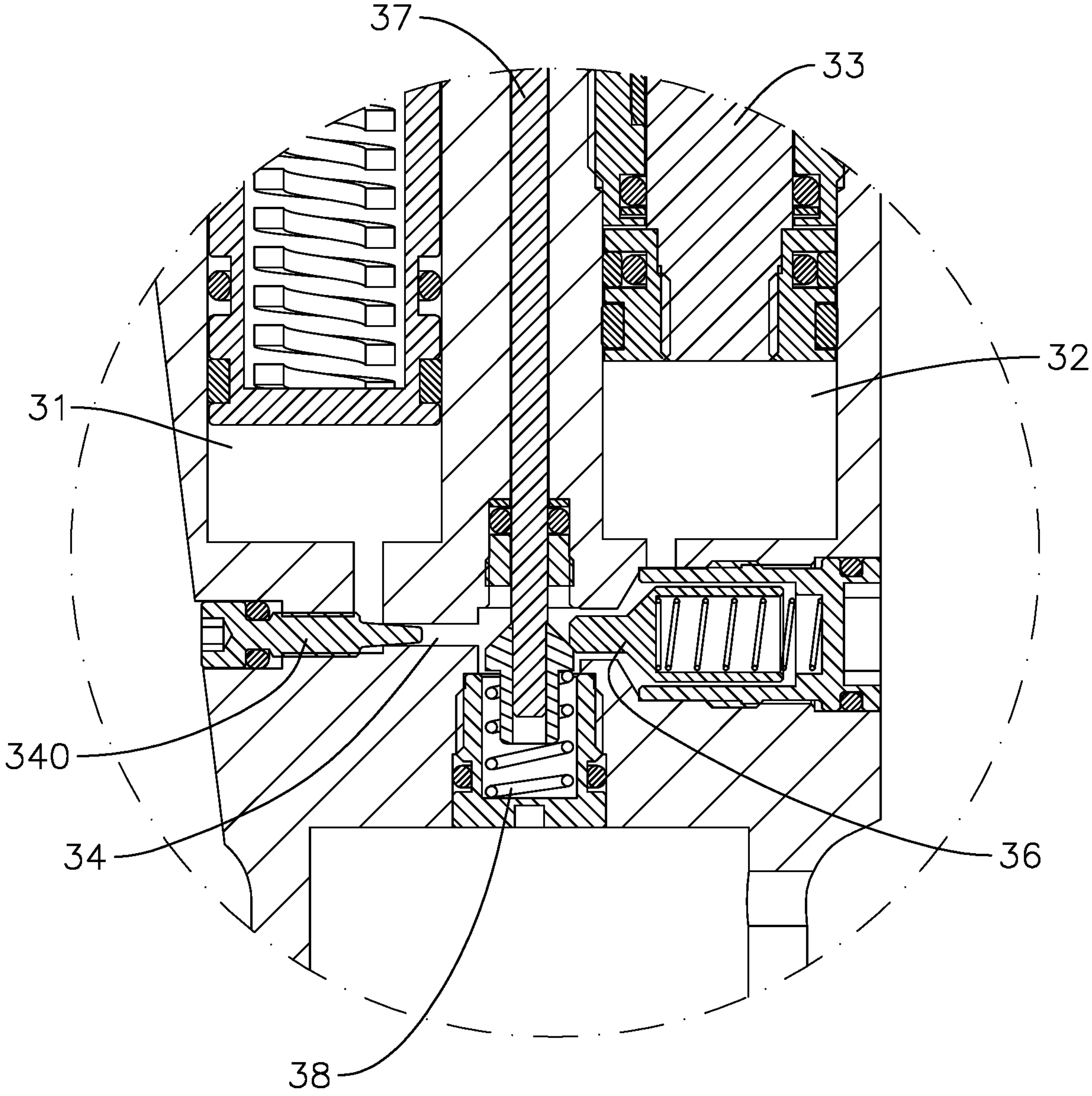
FIG. 6 is an enlarged view of the modular knee joint in FIG. 5.
Figure 7:
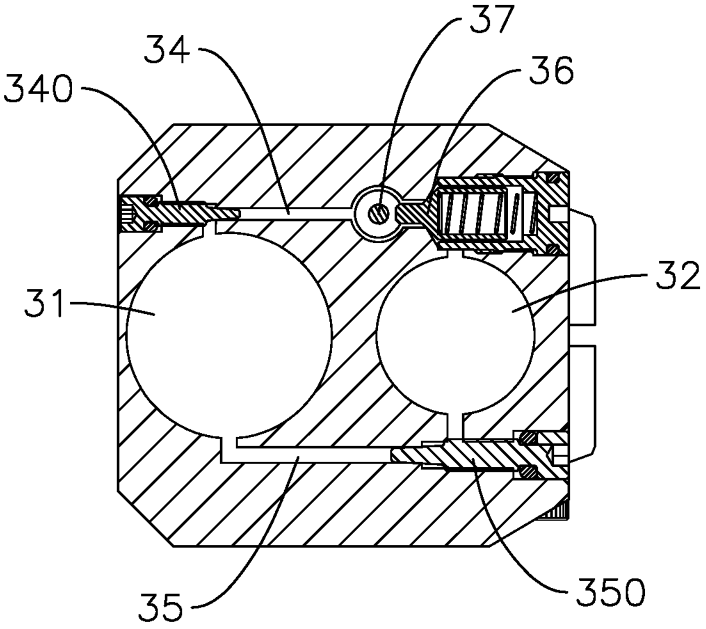
FIG. 7 is a sectional view of the modular knee joint across line 7-7 in FIG. 4.

With reference to FIG. 6 and FIG. 7, the lower connecting unit 12 is securely mounted on the actuating assembly 30. The actuating assembly 30 comprises a first oil storage cavity 31, a second oil storage cavity 32, a plunger shaft 33, a first connecting channel 34, a second connecting channel 35, a movable plug 36, and a driven unit 37. In this embodiment, the actuating assembly 30 also comprises a first regulating plug 340 and a second regulating plug 350. The plunger shaft 33 is mounted through the second oil storage cavity 32 and is pivoted on the third lower end of the third connecting rod 25. The first connecting channel 34 and the second connecting channel 35 fluidly communicate with the first oil storage cavity 31 and the second oil storage cavity 32.

The first regulating plug 340 is mounted through the first connecting channel 34 and can control a depth of the first regulating plug 340 penetrating into the first connecting channel 34. The first regulating plug 340 comprises a conical surface. By controlling the depth of the first regulating plug 340, a gap between the conical surface and an inner wall of the first connecting channel 34 can be adjusted, so the flow rate of hydraulic oil flowing between the first oil storage cavity 31 and the second oil storage cavity 32 can be adjusted. Similarly, the second regulating plug 350 is mounted through the second connecting channel 35 and can control a depth of the second regulating plug 350 penetrating into the second connecting channel 35. The second regulating plug 350 comprises a conical surface. By controlling the depth of the second regulating plug 350, a gap between the conical surface and an inner wall of the second connecting channel 35 can be adjusted, so the flow rate of hydraulic oil flowing between the first oil storage cavity 31 and the second oil storage cavity 32 can be adjusted.

The movable plug 36 selectively blocks the first connecting channel 34. An end of the driven unit 37 is connected to the connecting rod assembly 20 and another end of the driven unit 37 is selectively pushed against the movable plug 36. Precisely, the end of the driven unit 37 is connected to the first connecting rod 23 and another end of the driven unit 37 comprises an inclined plane. The inclined plane of the driven unit 37 is selectively pushed against the movable plug 36. In this embodiment, the actuating assembly 30 further comprises a driven elastic unit 38. The driven elastic unit 38 is connected to the driven unit 37 and tends to push the driven unit 37 against the movable plug 36.

With reference to FIG. 5 again, the locking assembly 40 selectively locks the connecting rod assembly 20. Therefore, the connecting rod assembly 20 cannot be pivoted. Precisely, the locking assembly 40 comprises a locking unit 41, an elastic unit 42, and a limiting unit 43. An end of the locking unit 41 is connected to the main connecting rod 21 and another end of the locking unit 41 is selectively pushed against the first connecting rod 23. An end of the elastic unit 42 is connected to the auxiliary connecting rod 22. Another end of the elastic unit 42 is connected to the locking unit 41 and tends to push the locking unit 41 against the first connecting rod 23. The limiting unit 43 is mounted on the main connecting rod 21 and located between the locking unit 41 and the first connecting rod 23.

With reference to FIG. 5 and FIG. 6, when the user's leg is straightened, that is, when the thigh and the prosthetic shank remain in a straight line, the upper connecting unit 11 and the lower connecting unit 12 also remain in a straight line. At this time, the limiting unit 43 blocks between the locking unit 41 and the first connecting rod 23, so the locking unit 41 and the first connecting rod 23 are not in contact. At the same time, the driven unit 37 is affected by the traction and the elastic force of the linked elasticity of the first connecting rod 23, and the inclined plane of the driven unit 37 abuts the movable plug 36, so the movable plug 36 cannot block the first connecting channel 34. When the first connecting channel 34 remains connected, the hydraulic oil in the second oil storage cavity 32 can easily flow into the second oil storage cavity 32 through the first connecting channel 34. In other words, the plunger shaft 33 can move freely within the second oil storage cavity 32 to change an internal volume of the second oil storage cavity 32, such that the user can easily bend the modular knee joint.

Figure 8:
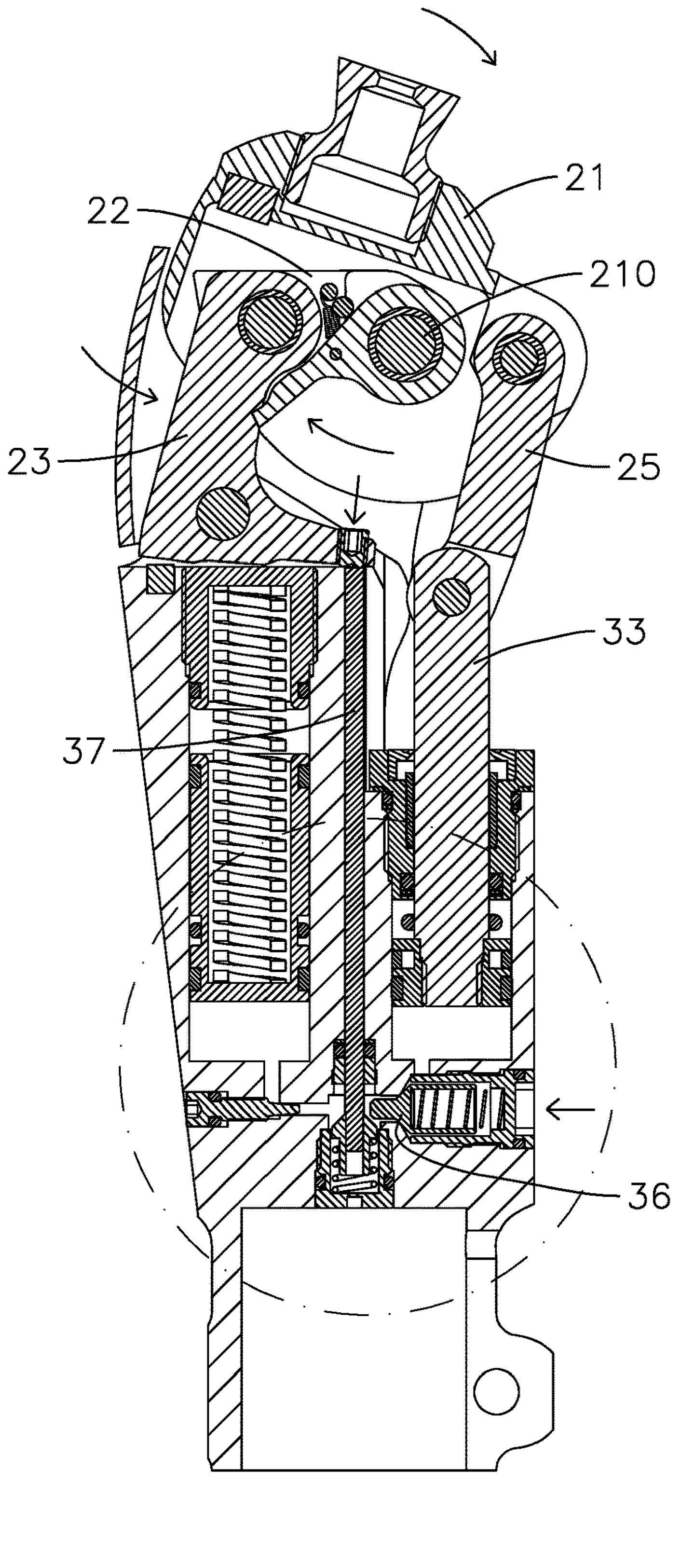
FIG. 8 is a sectional view of the modular knee joint after bending across line 5-5 in FIG. 4.
Figure 9:
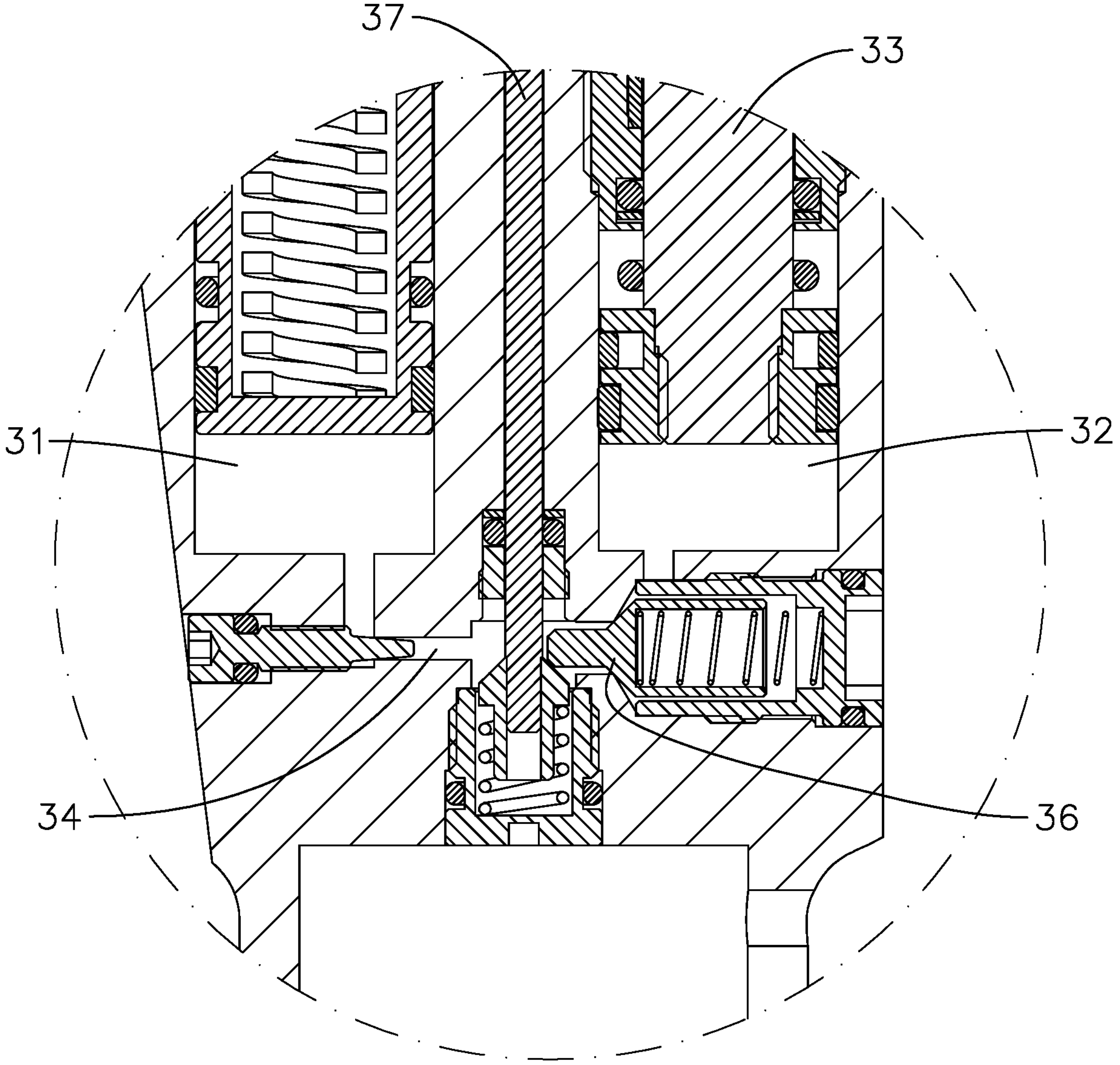
FIG. 9 is an enlarged view of the modular knee joint after bending in FIG. 8.

With reference to FIG. 8 and FIG. 9, when the user's leg is bended, the upper connecting unit 11 and the lower connecting unit 12 relatively rotate to an actuating angle, and the driven unit 37 and the movable plug 36 are separated by the connecting rod assembly 20. Precisely, when the upper connecting unit 11 and the lower connecting unit 12 relatively rotate to the actuating angle, the first connecting rod 23 rotates to engage with the locking unit 41 at the same time, such that the driven unit 37 keeps separating from the movable plug 36. When the first connecting rod 23 and the locking unit 41 engage with each other, the locking unit 41 is pushed against the first connecting rod 23, thereby preventing the first connecting rod 23 from continuing to rotate relatively to the main connecting rod 21. In other words, as long as the user bends the modular knee joint, no matter what the angle is, the locking unit 41 will engage with the first connecting rod 23.

When the driven unit 37 and the movable plug 36 are separated, the movable plug 36 can block the first connecting channel 34. At this time, the hydraulic oil can only flow from the second oil storage cavity 32 to the first oil storage cavity 31 through the second connecting channel 35. Since the gap of the second connecting channel 35 is small, the flow rate of the hydraulic oil through the second connecting channel 35 is very slow, such that the plunger shaft 33 cannot easily penetrate the second oil storage cavity 32, causing a resistance that prevents the user from further smooth bending. In other words, at this time, the connecting rod assembly 20 cannot pivot further, and the user's modular knee joint can maintain a slow bend.

After maintaining this posture for a period time, a certain amount of hydraulic oil can still flow to the first oil storage cavity 31 through the second oil storage cavity 32, allowing the plunger shaft 33 to penetrate the second oil storage cavity 32, so the bending angle of the user's modular knee joint can still slowly increase. That is, the user can keep the modular knee joint bending with the resistance during the entire bending process of the modular knee joint, and the modular knee joint will not lose the resistance after bending in a specific angle, so it can maintain the effect of gentle bending at all time.

Through the present invention, the bending process of the modular knee joint can be maintained at a slow bending. When the user wears the modular knee joint and goes down the stairs, the bending angle of the modular knee joint can be maintained when the foot with the modular knee joint is behind, such that the modular knee joint will not lose resistance and the user will not fall on the stairs. Similarly, the user can also walk smoothly when walking on uneven ground with height differences. Therefore, if the heel contacts the ground during walking, the resistance mechanism of the modular knee joint is turned on during the full-angle bending process and the modular knee joint can be maintained at a slow bending. In contrast, the resistance mechanism of the modular knee joint is turned off when the toes contact the ground during walking.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A modular knee joint configured to connect a thigh and a prosthetic shank of a user; the modular knee joint comprising:

an upper connecting unit configured to connect the thigh of the user;

a lower connecting unit configured to connect the prosthetic shank;

a connecting rod assembly located between the upper connecting unit and the lower connecting unit;

a locking assembly selectively locking the connecting rod assembly, therefore the connecting rod assembly incapable of pivoting;

an actuating assembly, the lower connecting unit securely mounted on the actuating assembly; the actuating assembly comprising:

a first oil storage cavity;

a second oil storage cavity;

a first connecting channel fluidly communicating with the first oil storage cavity and the second oil storage cavity;

a second connecting channel fluidly communicating with the first oil storage cavity and the second oil storage cavity;

a movable plug selectively blocking the first connecting channel; and a driven unit, an end of the driven unit connected to the connecting rod assembly, and another end of the driven unit selectively pushing the movable plug;

wherein when the upper connecting unit and the lower connecting unit rotate with respect to each other, the driven unit and the movable plug are separated by the connecting rod assembly; then the movable plug blocks the first connecting channel, and the locking assembly locks the connecting rod assembly at the same time; therefore, the connecting rod assembly is incapable of pivoting and the driven unit and the movable plug keep separated.

2. The modular knee joint as claimed in claim 1, wherein the connecting rod assembly comprises:

a main connecting rod, the upper connecting unit securely mounted on the main connecting rod, the main connecting rod comprising a main pivot shaft located between a front side of the main connecting rod and a back side of the main connecting rod;

a first connecting rod comprising a first upper end and a first lower end, the first upper end connected to the main connecting rod, and the first lower end pivotably mounted on the actuating assembly; an end of the driven unit connected to the first connecting rod;

a second connecting rod comprising a second upper end and a second lower end, the second upper end connected to the main pivot shaft of the main connecting rod, and the second lower end pivotably mounted on the actuating assembly; and an auxiliary connecting rod, an end of the auxiliary connecting rod pivotably mounted on the main pivot shaft of the main connecting rod, and another end of the auxiliary connecting rod pivotably mounted on the first upper end of the first connecting rod.

3. The modular knee joint as claimed in claim 2, wherein the locking assembly comprises:

a locking unit, an end of the locking unit connected to the main connecting rod, and another end of the locking unit selectively pushing the first connecting rod;

wherein when the upper connecting unit and the lower connecting unit rotate with respect to each other, the locking unit pushes the first connecting rod and thereby prevents the first connecting rod from rotating with respect to the main connecting rod.

4. The modular knee joint as claimed in claim 3, wherein, the locking assembly comprises:

an elastic unit, an end of the elastic unit connected to the auxiliary connecting rod, another end of the elastic unit connected to the locking unit, and the elastic unit configured to drive the locking unit to push the first connecting rod.

5. The modular knee joint as claimed in claim 3, wherein the locking assembly comprises:

a limiting unit mounted on the main connecting rod and located between the locking unit and the first connecting rod.

6. The modular knee joint as claimed in claim 4, wherein the locking assembly comprises:

a limiting unit mounted on the main connecting rod and located between the locking unit and the first connecting rod.

7. The modular knee joint as claimed in claim 2, wherein the connecting rod assembly comprises:

a third connecting rod comprising a third upper end and a third lower end, and the third upper end pivoted to the backside of the main connecting rod.

8. The modular knee joint as claimed in claim 6, wherein the connecting rod assembly comprises:

a third connecting rod comprising a third upper end and a third lower end, and the third upper end pivoted to the backside of the main connecting rod.

9. The modular knee joint as claimed in claim 7, wherein the actuating assembly comprises a plunger shaft mounted through the second oil storage cavity and connected to the third lower end of the third connecting rod.

10. The modular knee joint as claimed in claim 8, wherein the actuating assembly comprises a plunger shaft mounted through the second oil storage cavity and connected to the third lower end of the third connecting rod.

11. The modular knee joint as claimed in claim 1, wherein the driven unit comprises an inclined plane selectively pushing the movable plug.

12. The modular knee joint as claimed in claim 10, wherein the driven unit comprises an inclined plane selectively pushing the movable plug.

13. The modular knee joint as claimed in claim 1, wherein the actuating assembly comprises a driven elastic unit connected to the driven unit and configured to drive the driven unit to push the movable plug.

14. The modular knee joint as claimed in claim 12, wherein the actuating assembly comprises a driven elastic unit connected to the driven unit and configured to drive the driven unit to push the movable plug.

* * * * *